(12) United States Patent
Kubiak et al.

(10) Patent No.: US 10,289,895 B2
(45) Date of Patent: May 14, 2019

(54) METHOD AND DEVICE FOR DETERMINING A THREE-DIMENSIONAL DISTORTION

(71) Applicant: ISRA SURFACE VISION GMBH, Herten (DE)

(72) Inventors: Rolf Kubiak, Dortmund (DE); Christian Ripperda, Cologne (DE)

(73) Assignee: ISRA SURFACE VISION GMBH, Herten (DE)

( * ) Notice: Subject to any disclaimer, the term of this patent is extended or adjusted under 35 U.S.C. 154(b) by 22 days.

(21) Appl. No.: 14/886,422

(22) Filed: Oct. 19, 2015

(65) Prior Publication Data

US 2016/0110860 A1 Apr. 21, 2016

(30) Foreign Application Priority Data

Oct. 21, 2014 (DE) .................. 10 2014 115 331
Oct. 21, 2014 (DE) .................. 10 2014 115 336

(51) Int. Cl.
*G06K 9/00* (2006.01)
*G06T 7/00* (2017.01)
(Continued)

(52) U.S. Cl.
CPC ....... *G06K 9/00208* (2013.01); *G01N 21/455* (2013.01); *G01N 21/958* (2013.01);
(Continued)

(58) Field of Classification Search
CPC ............. G06K 9/00208; G01N 21/455; G01N 21/958; G01N 2021/9586; G06T 7/0067;
(Continued)

(56) References Cited

U.S. PATENT DOCUMENTS 8,064,069 B2 11/2011 Wienand et al.
8,224,066 B2 7/2012 Haeusler
(Continued)

FOREIGN PATENT DOCUMENTS

CN 1729381 A 2/2006
CN 102159917 A 8/2011
(Continued)

OTHER PUBLICATIONS

Estalella, Pau, A GPU-driven Algorithm for Accurate Interactive Reflections on Curved Objects. Tomas Akenine-Mollder and Wolfgang Heidrich, Eurographics Symposium on Rendering, Jun. 2006, Nicosie, Cyprus, ACM, p. 7, 2006.*
(Continued)

*Primary Examiner* — Chan S Park
*Assistant Examiner* — Elisa M Rice
(74) *Attorney, Agent, or Firm* — Collard & Roe, P.C.

(57) ABSTRACT

A method for determining a distortion of the image of an object formed by a reflection on a reflecting object includes capturing a reflected image of the reflecting object, determining, using the captured reflected image, a three-dimensional (3-D) shape of the surface of the reflecting object, calculating, based on the determined 3-D shape, distortion of the captured reflected image of the reflecting object from different viewing directions and using the calculated distortion from the different viewing directions, determining a three-dimensional (3-D) distortion of the surface of the reflecting object.

10 Claims, 1 Drawing Sheet

(51) Int. Cl.
*G01N 21/45* (2006.01)
*G01N 21/958* (2006.01)

(52) U.S. Cl.
CPC .... *G06T 7/0008* (2013.01); *G01N 2021/9586* (2013.01); *G06T 7/0004* (2013.01); *G06T 2207/10028* (2013.01)

(58) Field of Classification Search
CPC ............... G06T 7/0048; G06T 7/0008; G06T 2207/10028
See application file for complete search history.

(56) References Cited

U.S. PATENT DOCUMENTS

| | | | |
|---|---|---|---|
| 8,415,648 B2 | 4/2013 | Ehrick | |
| 8,861,831 B2 | 10/2014 | Le Moal et al. | |
| 2005/0254378 A1* | 11/2005 | Wagner | G01B 11/303 369/53.1 |
| 2008/0158239 A1 | 7/2008 | Lamy et al. | |
| 2010/0060905 A1* | 3/2010 | Wienand | G01B 11/25 356/612 |
| 2010/0201783 A1* | 8/2010 | Ueda | G02B 27/2228 348/46 |
| 2011/0228052 A1* | 9/2011 | Ohnishi | G01B 11/245 348/47 |

FOREIGN PATENT DOCUMENTS

| | | |
|---|---|---|
| CN | 102243074 | 6/2014 |
| DE | 10217068 | 5/2004 |
| DE | 012004033526 | 2/2006 |
| DE | 102006015792 | 10/2007 |
| DE | 102008023599 | 12/2008 |
| DE | 102013105570 | 12/2014 |
| EP | 0834837 | 4/1998 |
| EP | 2101143 | 9/2009 |
| FR | 2951544 | 4/2011 |
| JP | 5-272949 | 10/1993 |
| JP | 2007048084 | 2/2007 |
| JP | 2008-224341 | 9/2008 |
| JP | 2011-512533 | 4/2011 |
| KR | 10-2011-0059631 A | 6/2011 |
| WO | WO2009/102490 | 8/2009 |

OTHER PUBLICATIONS

United Nations Economic Commission for Europe (ECE) R43 Regulation, Aug. 29, 2012.
Denis Perard et al: "Three-Dimentional Measurement of Specular Free-From Surfaces With a Structured-Lighting . . . ".
Harding, Kevin G. & Svetkoff, Donald J. (Eds), SPIE vol. 3200277-786X, 1997, pp. 74-80. ISBN 978-08194256369.
Song, L. et al. "Surface profile measurement of specular cell phone cases on variable lateral scales by fringe reflection technique." Journal of Optoelectonics—Laser, vol. 23, No. 11, Nov. 2012, pp. 2154-2162 with English abstract.
Knauer, M.C. et al. "Measuring the refractive power with deflectometry in transmission" DGaO Proceedings 2008—http://www.dgao-proceedings.de—ISSN: 1614-8436, 2 pages.

\* cited by examiner

METHOD AND DEVICE FOR DETERMINING A THREE-DIMENSIONAL DISTORTION

CROSS-REFERENCE TO A RELATED APPLICATION

The invention described and claimed hereinbelow is also described in German Patent Application DE 10 2014 115 331.6, filed on Oct. 21, 2014, and in German Patent Application DE 10 2014 115 336.7, also filed on Oct. 21, 2014. The German Patent Applications, the subject matters of which are incorporated herein by reference, provide the basis for a claim of priority of invention under 35 U.S.C. 119(a)-(d).

BACKGROUND OF THE INVENTION

The present invention relates to a method for determining a distortion of the image of an object formed by a reflection on a reflective object, and to a device therefor.

When an object is mirrored in an object provided with a reflective surface, distortions such as dimensional changes, diminutions, enlargements or curvature changes result due, in particular, to irregularities on the surface of the object. The distortions cause the image of the object to have an appearance which differs from the actual appearance of the object.

When considering reflective objects such as mirror-finished facades or glass panes of automobiles, it is often required that the outside world be depicted on the reflective surface of this object with as little distortion as possible. Distortions in the depiction of an object often result in aesthetic problems for the reflective object itself. In the case of automobiles, for example, it should be ensured that a contour that is as constant as possible is perceived. Great distortions in reflection cause the observer to have an unacceptable perception of the automobile.

SUMMARY OF THE INVENTION

The present invention overcomes the shortcomings of known arts, such as those mentioned above.

The invention provides a simple, cost-effective and rapid method for evaluating distortions in an image of an object formed by a reflection on a reflective object and a simple and cost-effective device for carrying out this method.

In one embodiment, a method includes first determining a three-dimensional shape of the surface of the reflective object and then, on the basis of the known three-dimensional shape of the surface, calculating distortion of the image of the object from different lines of sight. On the basis of the distortion of the image of the object from different lines of sight, a three-dimensional distortion is determined.

The invention is based on a finding that optical distortions in reflection are caused by curvatures and, in particular, by changes in curvatures. Great changes in curvatures, in particular over a short distance, result in an apparent movement of a reflective object when the viewing angle changes, e.g., due to a movement of the reflective object relative to the observer. The curvatures or changes in curvatures in the surface of the reflective object also can be described as a change in the refractive index at this point.

According to the invention, the three-dimensional shape of the surface of the reflective object is therefore determined first. The three-dimensional shape of the surface includes the information regarding the curvatures of the surface at all the points thereof. The curvatures at a specific point on the surface of the object correspond to the particular refractive indices at this point.

In an embodiment, the three-dimensional shape of the surface of the reflective object, and therefore the curvatures of the surface at each point, are determined by deflectometry with the aid of a camera. Deflectometric measurements are used to ascertain the three-dimensional shape of the object without the need for reference marks. To this end, a preferable approach in the case of large reflective objects having a large surface is to first measure the reflective object in sections using a plurality of cameras. On the basis of these measured values, the topography is used to computationally compose a three-dimensional overall shape of the surface.

As an alternative, the three-dimensional shape of the surface of the reflective object is determined by use of reference marks, by purely mechanical, tactile measurements, or by measurement of diffusively reflective surfaces via triangulation.

As described above, the refractive powers at this point can be computationally determined on the basis of the curvatures of the reflective object, which are effective for a certain line of sight and a certain point on the surface. In this context, it was recognized that the refractive powers, which can be calculated on the basis of the curvatures, change when the observer looks at the reflective object from different viewing angles. It is therefore possible to determine effects with regard to distortion, which are caused by changing the viewing angle, on the basis of the known three-dimensional topography of the object. In the calculation, it is therefore assumed that a virtual camera is disposed in every desired viewing direction. The reflected image of the object is then determined from the perspective of such a virtual camera. The distortions of the object image which result from different viewing angles are also referred to collectively as three-dimensional distortion.

The method according to the invention has the advantage that the three-dimensional distortion is determined after only one measurement of the reflective object. The method according to the invention minimizes the time required to evaluate a reflective object with regard to the three-dimensional distortion thereof, since it is only necessary to determine the three-dimensional topography of the reflective object. Due to the method according to the invention, it is no longer necessary to reconfigure a measuring device for determining a three-dimensional distortion using real cameras from different viewing angles, and therefore the time required to evaluate a reflective object is also minimized.

Another advantage of the method according to the invention is that the method can be used for any types of objects to be imaged. The object can be a rectangular lattice, for example, or any type of two- or three-dimensional object.

Furthermore, the distortion can be investigated for any viewing angle with respect to the surface of the reflective object. The method according to the invention is therefore highly flexible and can be rapidly adapted to the different viewing-angle requirements specified by a specific customer.

The method according to the invention is preferably used within the scope of automated quality testing of reflective objects. As described above, to this end, the three-dimensional shape of the surface is determined and, on the basis thereof, the three-dimensional distortion is automatically determined on the basis of the requirements of the particular customer with regard to the reflective object, e.g. with regard to the viewing angle and/or shape and/or position of the object. The distortion data are then compared with the customer's requirements with regard to distortion. Depending on the comparison of the ascertained distortion data based on the three-dimensional shape of the surface with the specified distortion data, it is then decided whether the reflective object meets the quality requirements of the particular customer. If the reflective object does not meet the customer's quality requirements, an error is reported, for example (e.g. an error is optically and/or acoustically indicated) and/or the particular object is removed from the production process.

Within the scope of the method according to the invention, the reflective objects do not necessarily need to have 100% reflectance, since this can vary within the scope of calculating the three-dimensional distortion. The reflectance of the reflective object can be set to any value, e.g. 100%. In this case, reflectance refers to the ratio of reflected light intensity to incident light intensity. The method according to the invention even makes it possible to allocate a reflectance of 100% to non-reflective objects and investigate the three-dimensional distortion.

The invention also provides a device, which is designed to first determine the three-dimensional shape of the surface of the reflective object (e.g. by means of a suitable determination device) and then, on the basis of the known three-dimensional shape of the surface, to calculate the distortion of the image of the object from various other viewing directions using a computing unit. Based on the calculated from the various other viewing directions, the three-dimensional distortion is determined.

The device calculates the distortion of the image of the object from different viewing directions, wherein, to this end, the computing unit disposes a virtual camera in every desired viewing direction and determines the reflected image of the object from the perspective of this virtual camera on the basis of the data on the three-dimensional shape of the surface.

A determination device of the inventive device according to the invention determines the shape of the surface of the object with the aid of a camera, preferably by means of deflectometry. In an embodiment, the determination device is part of the computing unit.

The computing unit of the device is furthermore designed to determine the distortion of the image of the object in a viewing direction which, at that particular point, corresponds to the normal on the surface of the object, for every point on the surface.

In addition, the reflectance of the surface of the object is varied by the computing unit.

The device according to the invention has the same advantages as the aforementioned method and is designed to carry out the aforementioned method steps.

The results that are determined can be used to evaluate, e.g. within the scope of quality testing, reflective objects (or non-reflective objects), for example glass panes of automobiles or facade panes, according to the criteria shape, dimensional change, curvature, curvature change and enlargement or diminution of objects when reflected. To this end, different limit values are checked by the inventive method and device, which limit values are specified in different requirement catalogs from the customer for producing reflective objects of this type.

In an embodiment, the distortion of the object image is determined in a viewing direction which corresponds to the surface normal at a specific point (=impact point of the view ray on the surface), for each point on the surface of the reflective object. A method of this type is advantageous, in particular, with regard to industrial products which are reflective objects, since it is hereby possible to determine the minimal optical effects which are unavoidably defined by the shape of the reflective object.

BRIEF DESCRIPTION OF THE DRAWINGS

Further features and advantages of the invention will become apparent from the description of embodiments that follows, with reference to the attached figures, wherein.

DETAILED DESCRIPTION OF THE PREFERRED EMBODIMENTS

The following is a detailed description of example embodiments of the invention depicted in the accompanying drawings. The example embodiments are presented in such detail as to clearly communicate the invention and are designed to make such embodiments obvious to a person of ordinary skill in the art. However, the amount of detail offered is not intended to limit the anticipated variations of embodiments; on the contrary, the intention is to cover all modifications, equivalents, and alternatives falling within the spirit and scope of the present invention, as defined by the appended claims.

Figure 1:
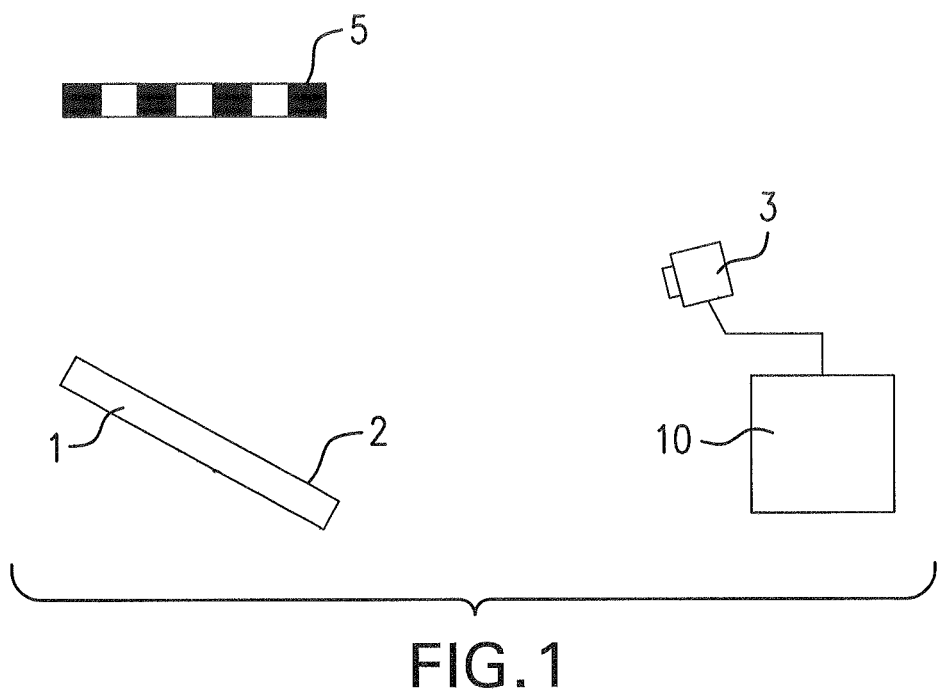
FIG. 1 presents a view from the side of a first subsystem of a device configured according to the invention for determining a three-dimensional distortion.

FIG. 1 depicts a reflective object in the form of a glass pane 1 for a window of an automobile. The glass pane has a reflective surface 2 which is observed by a camera (real camera) 3. In particular, the camera 3 observes the image of an object formed via reflection on the surface 2 of the glass pane 1, which object is in the form of a lattice such as a regular or square lattice 5. Any other type of functionally equivalent object also can be used for the deflectometric measurement. In the case of a large glass pane 1, it is also possible to use a plurality of cameras, which detect different regions of the surface of the glass pane 1.

The three-dimensional shape of the surface 2 of the glass pane 1 is determined using deflectometry using a determination device of the device according to the invention on the basis of the image of the object captured by the camera 3. The determination device is part of or embodies a computing unit 10, including a memory, which is shown connected to camera 3. Please note that the connection of computing unit 10 is not limited to a hardwire connection to camera 3 as shown, but also may be connected wirelessly. When a plurality of cameras is used, the different measurements are used to compose the three-dimensional shape of the surface 2 of the glass pane 1.

Figure 2:
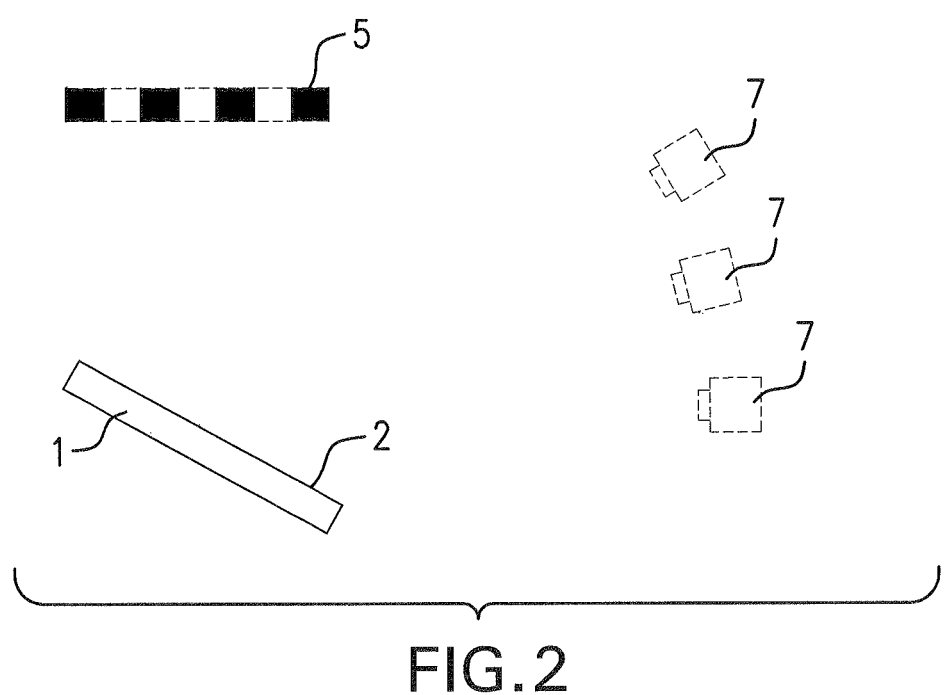
FIG. 2 shows a second subsystem of a device configured according to the invention.

In order to determine the three-dimensional distortion of the lattice 5, the device according to the invention then calculates the distortion of the lattice 5 from the different viewing directions using a suitably designed computing unit, as shown in FIG. 2, on the basis of the ascertained three-dimensional shape of the surface 2, the resultant curvatures at all points on the surface 2 and refractive powers from different viewing directions. To this end, the computing unit assumes that a virtual camera 7 views the reflective object 1 from the particular viewing direction. On the basis thereof, the image of the (virtual) lattice 5, and the distortion thereof, is calculated while this lattice 5 is reflected on the surface 2 of the object 1, e.g., by ray tracing. On the basis thereof, the computing unit determines distortion effects when the viewing angle changes, i.e., the three-dimensional distortion. The lattice 5 is also provided as a virtual lattice for calculating the three-dimensional distortion.

Within the scope of a quality inspection, the computing unit compares the ascertained three-dimensional distortion of the glass pane with the customer's requirements and makes a decision (determination) as to whether the ascertained distortion of the glass pane 1 meets the requirements. If this is not the case, the glass pane 1 is removed from the production process.

LIST OF REFERENCE NUMBERS

1 glass pane
2 surface of the glass pane
3 camera
5 lattice
7 virtual camera
10 computing unit As will be evident to persons skilled in the art, the foregoing detailed description and figures are presented as examples of the invention, and that variations are contemplated that do not depart from the fair scope of the teachings and descriptions set forth in this disclosure. The foregoing is not intended to limit what has been invented, except to the extent that the following claims so limit that.

What is claimed is:

1. A method for determining a distortion in the image of an object formed by a reflection on a reflector, the method comprising the steps of:
    capturing an image of the object reflected by the reflector;
    using the captured reflected image for determining a three-dimensional (3-D) shape of the surface of the reflector;
    based on the determined 3-D shape, calculating the distortions of the images of the object formed by the reflection by the reflector from a plurality of different viewing directions; and
    using the calculated distortion from the plurality of different viewing directions, determining a three-dimensional (3-D) distortion in the image of the object formed by reflection on the reflector, wherein the step of calculating distortions from the different viewing directions includes assuming that a virtual camera is disposed in every direction of the different viewing directions and that one virtual image of the object reflected by the reflector is determined from each perspective of the virtual camera.

2. The method according to claim 1, wherein the step of capturing the image of the object reflected by the reflector is implemented with a camera and wherein the step of determining the 3-D shape of the surface of the reflector is implemented using deflectometry.

3. The method according claim 1, wherein the step of determining the 3-D distortion in the image of the object formed by reflection on the reflector is implemented in a viewing direction of the different viewing directions that corresponds to a direction normal to the surface of the reflector, for every point on the surface.

4. The method according to claim 1, further comprising varying a reflectance of the surface of the reflector.

5. The method according to claim 1, further comprising assessing the calculated 3D distortion in the image of an object formed by reflection on the reflector in order to determine whether the calculated 3D distortion is within an acceptable range specified therefor.

6. The device according to claim 5, wherein of the reflectance of the surface of the reflector is varied.

7. A device for determining a three-dimensional (3-D) distortion in an image of an object formed by a reflection on a reflector, comprising:
    a camera for capturing the image of the object reflected by the reflector;
    a determination device for determining, from the captured image of the object, a three-dimensional (3-D) shape of a surface of the reflector;
    a computing unit for calculating, on the basis of the determined shape of the 3-D shape of the surface of the reflector, the distortions in the images of the object formed by the reflection by the reflector from a plurality of different viewing directions and according to the calculated distortions from the different viewing directions, calculating a three-dimensional (3-D) distortion in the image of the object formed by reflection on the reflector,
    wherein the computing unit calculates the distortions from the different viewing directions in reliance upon a virtual camera virtually positioned in order to virtually capture the image of the object formed by reflection on the reflector from each of the different viewing directions and to determine the reflected image of the object reflected by the reflector from each perspective of the virtual camera.

8. The device according to claim 7, wherein the determination device determines the shape of the surface of the reflector using deflectometry.

9. The device according to claim 7, wherein the computing unit calculates the distortion in the image of the object formed by reflection on the reflector in a viewing direction of the different viewing directions, wherein the viewing direction corresponds to a direction that is normal on the surface of the reflector for every point on the surface.

10. The device according to claim 7, wherein the computing unit assesses the calculated 3-D distortion in the image of the object formed by reflection on the reflector to determine whether the calculated 3D distortion is within an acceptable range specified therefor.

* * * * *